(12) United States Patent
Suzuki et al.

(10) Patent No.: US 8,048,112 B2
(45) Date of Patent: Nov. 1, 2011

(54) ROD FIXING APPARATUS FOR VERTEBRA CONNECTING MEMBER

(75) Inventors: Nobumasa Suzuki, Tokyo (JP); Yutaka Nohara, Koshigaya (JP); Shinnosuke Nakahara, Okayama (JP); Shigenobu Sato, Sapporo (JP); Kazumasa Ueyama, Hirosaki (JP); Kazuhiro Hasegawa, Niigata (JP); Kazuya Oribe, Tokyo (JP); Hiroshi Takamido, Nagoya (JP)

(73) Assignee: Showa IKA Kohgyo Co., Ltd., Aichi-Ken (JP)

( * ) Notice: Subject to any disclaimer, the term of this patent is extended or adjusted under 35 U.S.C. 154(b) by 1909 days.

(21) Appl. No.: 10/659,302

(22) Filed: Sep. 11, 2003

(65) Prior Publication Data

US 2004/0122425 A1   Jun. 24, 2004

(30) Foreign Application Priority Data

Sep. 12, 2002   (JP) ................... P2002-267298

(51) Int. Cl.
*A61B 17/70* (2006.01)
(52) U.S. Cl. .............. 606/246; 606/266; 606/270
(58) Field of Classification Search ........... 606/61, 606/72, 73, 246, 264–278
See application file for complete search history.

(56) References Cited

U.S. PATENT DOCUMENTS

| | | | |
|---|---|---|---|
| 5,024,213 A | 6/1991 | Asher et al. | |
| 5,257,993 A | 11/1993 | Asher et al. | |
| 5,346,493 A | 9/1994 | Stahurski et al. | |
| 5,443,467 A | 8/1995 | Biedermann et al. | |
| 5,496,321 A * | 3/1996 | Puno et al. .......... | 606/61 |
| 5,520,689 A | 5/1996 | Schlapfer et al. | |
| 5,562,663 A * | 10/1996 | Wisnewski et al. ......... | 606/61 |
| 5,643,261 A * | 7/1997 | Schafer et al. .......... | 606/61 |
| 5,984,923 A | 11/1999 | Breard | |
| 6,077,262 A | 6/2000 | Schläpfer et al. | |
| 6,110,172 A * | 8/2000 | Jackson .......... | 606/61 |
| 6,485,494 B1 * | 11/2002 | Haider .......... | 606/73 |
| 6,540,749 B2 * | 4/2003 | Schafer et al. .......... | 606/61 |
| 6,613,049 B2 * | 9/2003 | Winquist et al. .......... | 606/59 |
| 6,620,164 B2 | 9/2003 | Ueyama et al. | |
| 6,652,526 B1 * | 11/2003 | Arafiles .......... | 606/61 |
| 2002/0040223 A1 | 4/2002 | Sato | |
| 2002/0111628 A1 * | 8/2002 | Ralph et al. .......... | 606/61 |

FOREIGN PATENT DOCUMENTS

| | | |
|---|---|---|
| DE | 4110002 | 5/1992 |
| EP | 0384001 | 8/1990 |
| EP | 0535623 | 4/1993 |
| EP | 1192911 | 4/2002 |

(Continued)

OTHER PUBLICATIONS

English Language Abstract of JP 11-509453.

(Continued)

*Primary Examiner* — Thomas Barrett
*Assistant Examiner* — Michael Araj
(74) *Attorney, Agent, or Firm* — Greenblum & Bernstein P.L.C.

(57) ABSTRACT

The fixing apparatus includes a pressure fixing device to pressure fix a rod to a circular arc rod engagement portion, and small protruding portions that bite into the rod and have an acute angle in both end sides of the rod engagement portion outside of the pressure fixing device. A recess surface of the circular arc rod engagement portion between the small protruding portions is formed as a rough surface.

3 Claims, 5 Drawing Sheets

FOREIGN PATENT DOCUMENTS

| | | |
|---|---|---|
| JP | 11509453 | 8/1999 |
| JP | 2001-245896 | 9/2001 |
| WO | 95/13756 | 5/1995 |
| WO | 01/91656 | 12/2001 |

OTHER PUBLICATIONS

English Language Abstract of DE 4110002.
English language Abstract of JP 2001-245896.

* cited by examiner

FIG.2A
FIG.2B
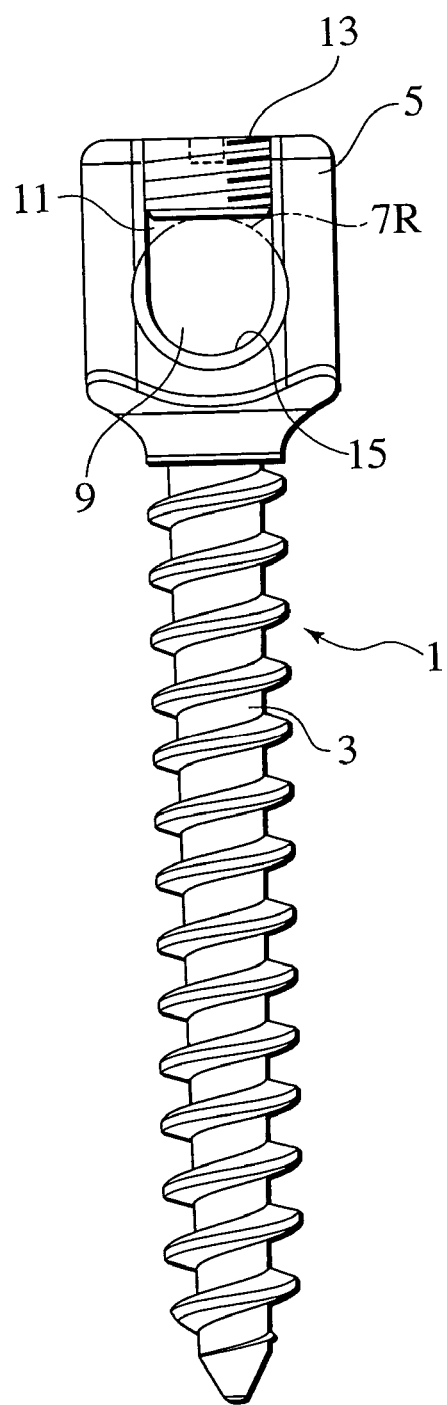
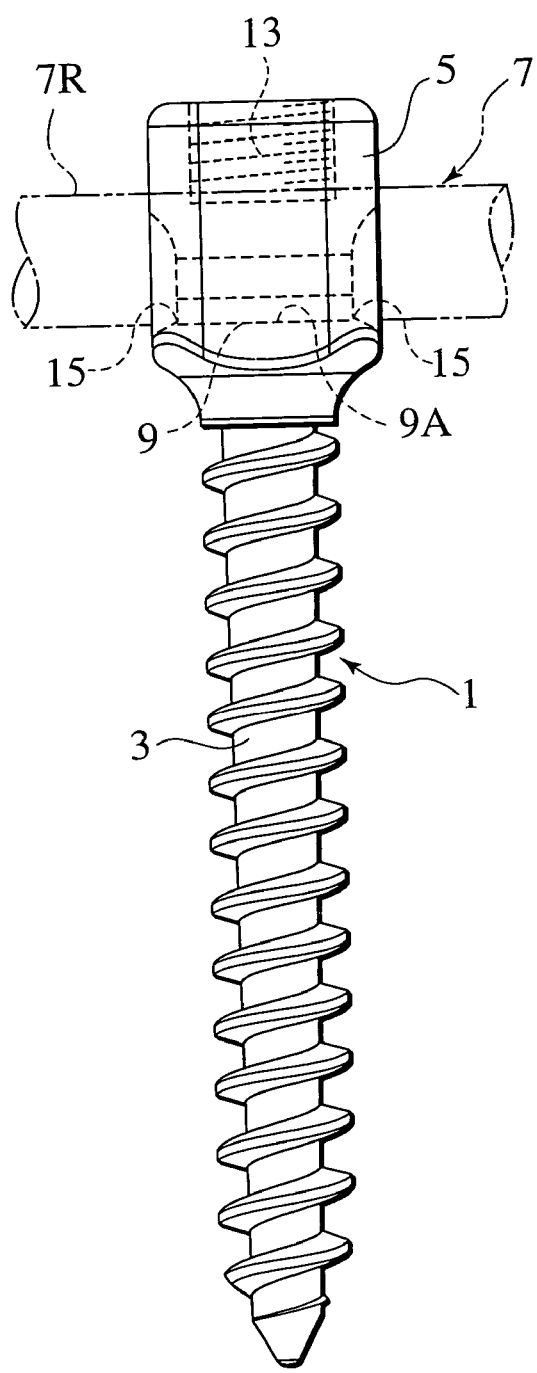

ROD FIXING APPARATUS FOR VERTEBRA CONNECTING MEMBER

CROSS REFERENCE TO RELATED APPLICATIONS

This application is based upon and claims the benefit of priority from the prior Japanese Patent Application No. P2002-267298, filed on Sep. 12, 2002; the entire contents of which are incorporated herein by reference.

BACKGROUND OF THE INVENTION

1. Field of the Invention

The present invention relates to a rod fixing apparatus (a rod fixing structure) fixing a rod portion of a rod member for integrally connecting a vertebra in an acantha, and more particularly to a rod fixing apparatus (a rod fixing structure) to prevent a rod portion of a rod member from being displaced in an axial direction and from being displaced in a rotating direction around an axis.

2. Description of the Related Art

A conventional rod fixing apparatus (fixing structure) is comprised of a screw having a screw portion screwed into a vertebra body in the vertebra, and a head portion integrally provided with the screw. The head portion further includes a groove being engaged with a rod portion of a connection member (a rod member) connecting the separated vertebra bodies, and a rod engagement portion such as an elongated-hole or the like. The rod engagement portion is provided with a pressure fixing device (a fastening screw or the like) for pressure fixing the rod portion engaged with the rod engagement portion.

According to the structure mentioned above, since a position of the rod portion may be displaced with respect to the head portion of the screw, it is necessary to prevent the rod portion from being displaced.

To prevent the rod portion from being displaced, a rod fixing apparatus 103 of a related art (refer to National Publication of Translated Version No. 11-509453) is comprised of a head portion 105 having a screw portion 101 being screwed into the vertebra body (not shown), and the head portion 105 further is comprised of a groove-shaped rod engagement portion 107 having a enlarged-engagement portion 109 being engaged with a enlarged convex rod portion 113 of a rod 111 (refer to FIGS. 1A, 1B).

According to this structure, it is possible to prevent the connection member 111 from being displaced in an axial direction from the rod connecting portion 107 of the head portion 105. However, it is necessary to match a position of the screw 103 and a position of the enlarged convex rod portion 113. Furthermore, it is complicated to manufacture the connection member 111 with the enlarged convex portion 113, and it is impossible to apply the structure to the conventional general rod.

SUMMARY OF THE INVENTION

The present invention is made by taking the conventional problem mentioned above into consideration, and to solve the above-mentioned problems, the present invention is a rod fixing apparatus (a rod fixing structure) for a vertebra connecting member for connecting separated vertebras, which is comprised of a pressure fixing device for pressure fixing a rod portion to a circular arc rod engagement portion engaging with the rod portion, and protruding portions eating into the rod portion in both end sides of the rod engagement portion outside the pressure fixing device.

BRIEF DESCRIPTION OF DRAWINGS

FIGS. 2A and 2B are schematic views showing a first embodiment of the present invention.

DETAILED DESCRIPTION OF THE INVENTION

Figure 1A:
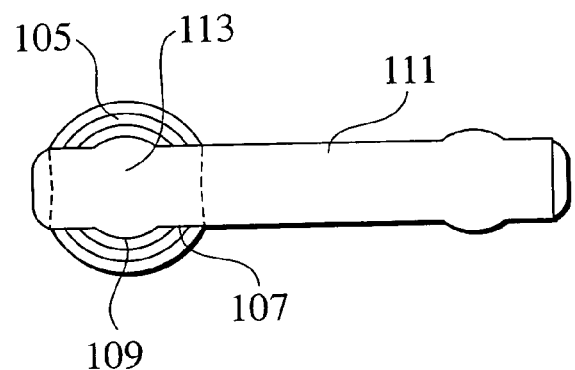
FIGS. 1A and 1B are schematic views of a prior art.
Figure 1B:
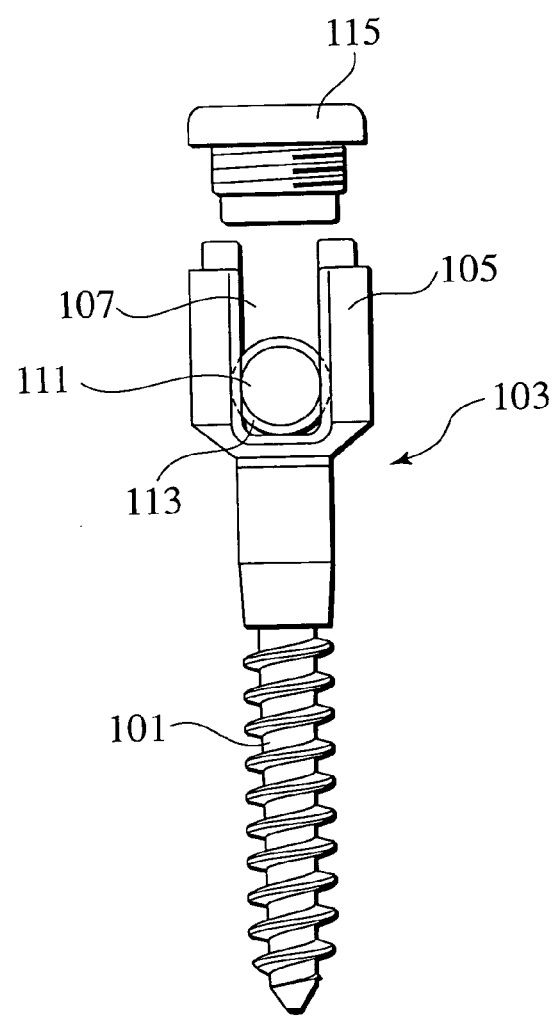

A description will be given below of embodiments according to the present invention with reference to FIGS. 2A to 5.

First Embodiment

In FIGS. 2A and 2B, a rod fixing apparatus (an implant) having a screw screwed into a vertebra is shown as one embodiment of an implant for fixing a vertebra connecting member. The fixing apparatus is not limited to the one having a screw, and can be applied to an implant having a hook provided with an engagement portion engaged with an arch of vertebra of the vertebra or a processus spinosus.

A fixing apparatus 1 of a first embodiment of the present invention is provided with a screw portion 3 screwed into a vertebra body of the vertebra (not shown) and a head portion 5 integrally formed with the screw 3. The head portion 5 is further comprised of an engagement hole (groove) of an engagement groove 11 having a circular arc rod engagement portion 9 freely engaged with a rod portion 7R of a vertebra connection member 7. In more detail, the rod engagement portion 9 is formed in a bottom portion of the engagement groove 11, and is formed in a half circular arc corresponding to a diameter of the rod portion 7R of the vertebra connection member 7 to be fixed.

Further, a pressure fixing device (a fixing screw) 13 for pressure fixing the rod portion 7R of the vertebra connection member 7 engaged with the engagement groove 11 to the rod engagement portion 9 is detachably screwed with the engagement groove 11. When the rod portion 7R is firmly pressure fixed by the fixing screw 13, an acute small protruding portion 15 eats into the rod portion 7R. The small protruding portion 15 is formed in each of both end portions of the rod engagement portion 9 in an outer side of the fixing screw 13. Further, a recess surface 9A of the rod engagement portion 9 between a pair of small protruding portions 15, 15 is formed in a rough surface so that a friction at a time when the rod portion 7R is brought into contact therewith becomes large, for example, by a sand blast or the like.

According to the structure of the first embodiment of the present invention, when the screw portion 3 of the fixing apparatus 1 being screwed into the vertebra body of the vertebra, engaging the rod portion 7R of the vertebra connection member 7 with the engagement groove 11 provided in the head portion 5 of the fixing apparatus 1, and pressure fixing the rod portion 7R to the rod engagement portion 9 in the bottom portion of the engagement groove 11, the rod portion 7R is fixed by the small protruding portions 15, 15 provided in both end sides of the rod engagement portion 9 and the fixing screw 13. When the small protruding portions 15, 15 bites the rod portion 7R firmly, it bites at a small amount enough to generate a scratch on a surface of the rod portion 7R, the rod portion 7R is bent at a small amount between both the small protruding portions 15, 15, and the rod portion 7R is brought into contact with the recess surface (the rough surface) 9A of the rod engagement portion 9.

According to the manner mentioned above, it is possible to prevent the rod portion 7R of the vertebra connection member 7 from being displaced in a longitudinal direction with respect to the head portion 5, and prevent the rod portion 7R from being displaced on the basis of a rotation of the rod portion 7R around an axis, respectively. Further, the rod portion 7R may be formed in a simple round rod shape, and it is possible to engage and fix a desired position of the rod portion 7R. In other words, it is not necessary to provide the conventional enlarged convex portion 113.

Second Embodiment

Figure 3:
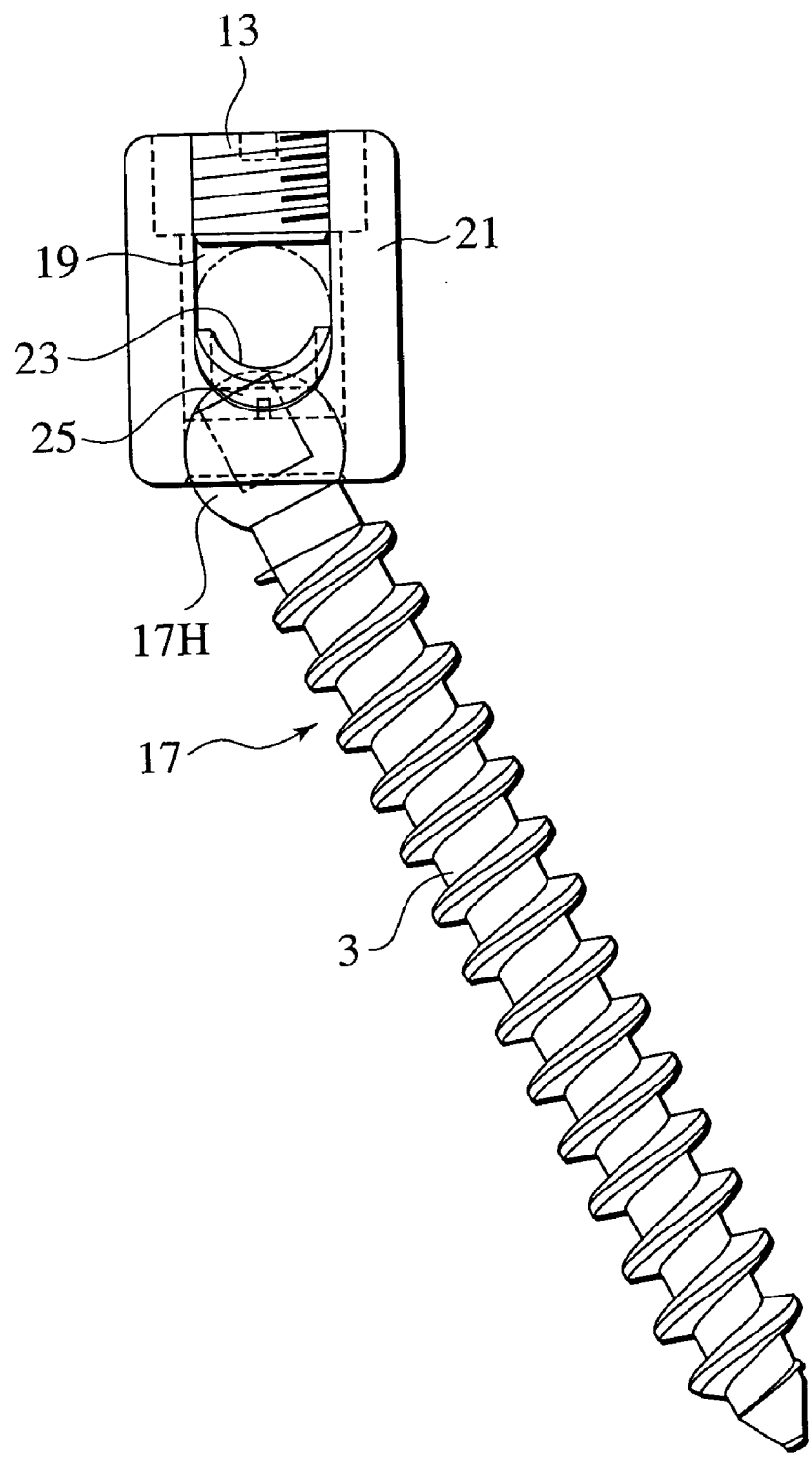
FIG. 3 is a schematic view showing a second embodiment of the present invention.
Figure 4A:
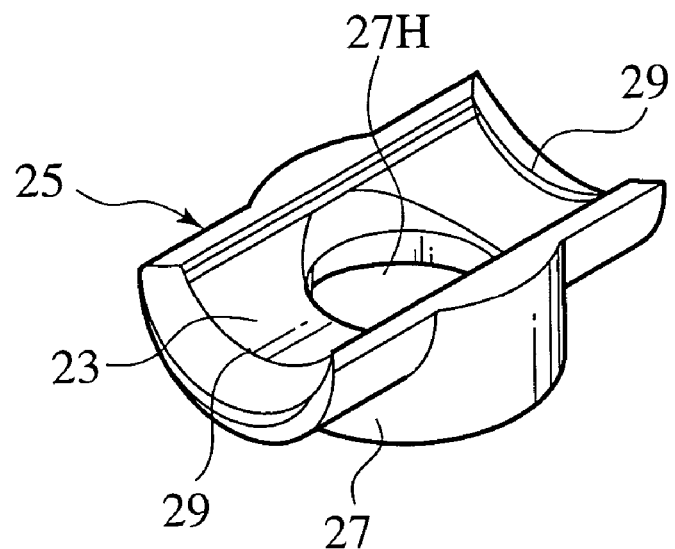
FIGS. 4A and 4B are partly enlarged views of a second embodiment of the present invention.
Figure 4B:
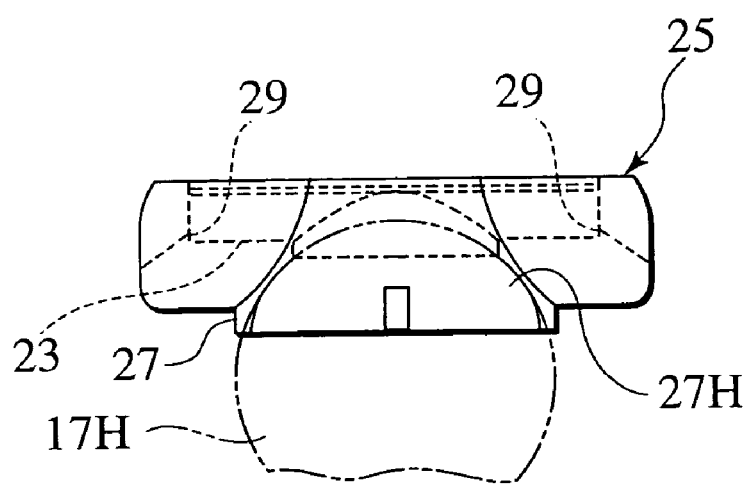

FIGS. 3, 4A and 4B show a second embodiment according to the present invention. In the second embodiment, the same reference numerals are attached to the constituting parts achieving the same functions as those of the first embodiment, and a overlapping description will be omitted.

In the second embodiment, a fixing apparatus 17 is comprised of the screw portion 3 having a globular head portion 17H, and an engagement head portion 21 having an engagement groove 19 (corresponding to the engagement groove 11 of the first embodiment) being engaged with the globular head portion 17H. A bottom portion of the engagement groove 19 is provided with a bottom member 25 having a canaliculate rod engagement portion 23 in which a contact surface with the rod portion (not shown here) is formed in a rough surface.

The bottom member 25 is structured such that the canaliculate rod engagement portion 23 is provided in an upper portion of a tubular engagement and protruding portion 27 having a hollow hole 27H being engaged with the head portion 17H of the fixing apparatus 17, and small protruding portions 29 (corresponding to the small protruding portions 15 of the first embodiment) are formed in both end portions of the rod engagement portion 23 (refer to FIGS. 4A and 4B).

According to the structure of the second embodiment, it is possible to swing the engagement head portion 21 in a desired direction with respect to the fixing apparatus 17, and it is possible to easily correspond to an incline of the rod portion 7R of the vertebra connection member 7 (refer to FIG. 2B).

According to the structure mentioned above, the small protruding portion 29 provided in the rod engagement portion 23 of the bottom member 25 eats into the rod portion 7R (not shown in FIGS. 3 to 4B) by engaging the rod portion 7R of the vertebra connection member 7 with the engagement groove 19 and fastening the fixing screw 13, so that the same effects as those of the first embodiment can be attained. Further, when firmly fastening the fixing screw 13, the portion of the hollow hole 27H of the bottom member 25 is firmly pressure fixed to the head portion 17H of the fixing apparatus 17, and it is possible to fix and support the vertebra connection member 7 to a predetermined position.

Third Embodiment

Figure 5:
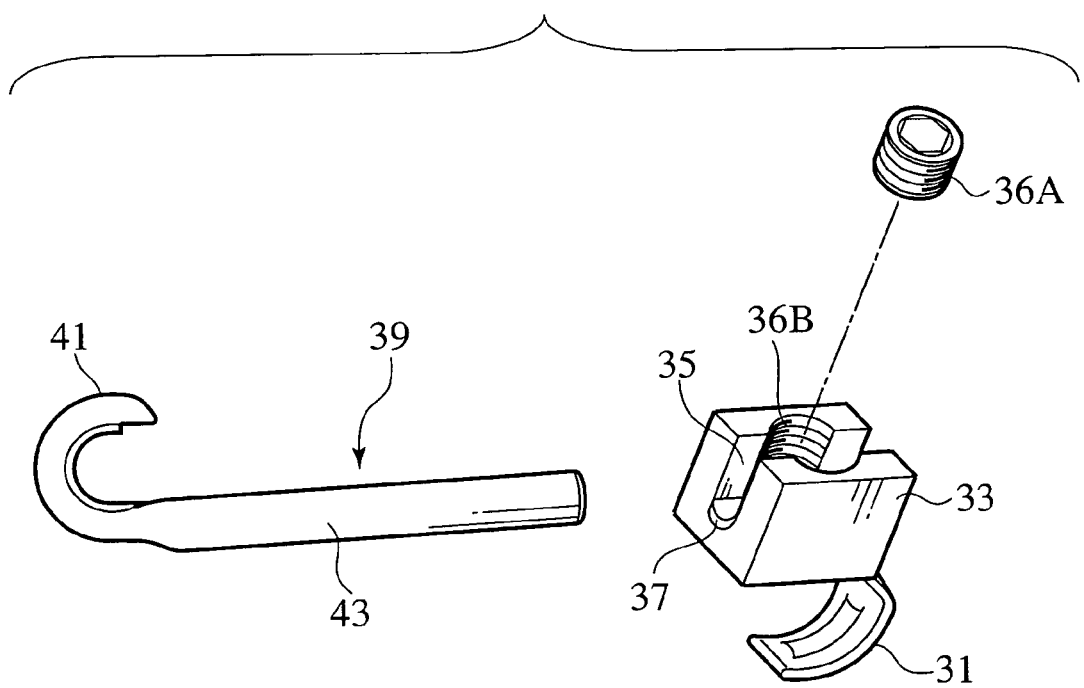
FIG. 5 is a schematic view showing a third embodiment of the present invention.

A third embodiment of this invention will be described below with reference to the accompanying FIG. 5.

A fixing apparatus (fixing structure) according to the third embodiment is comprised of a hook 31 freely hooked to an arch of vertebra (not shown) in the vertebra (not shown), a block 33 (a main element of the apparatus) integrally provided with the hook 31 and having an engagement groove 35 (corresponding to the engagement groove 11 of the first embodiment) and a female screw portion 36B freely engaging a fixing screw 36A. The engagement groove 35 further includes small protruding portions 37 (corresponding to the small protruding portions 15 of the first embodiment) provided on both end sides of a bottom portion on a rough surface of the engagement groove 35. Further, as a vertebra connection member 39, a hook 41 freely hooked to a processus spinosus (not shown) in the vertebra is provided in a front end portion of a rod portion 43.

According to the structure mentioned above, the same effects as those of the first and second embodiments can be attained by engaging the rod portion 43 of the vertebra connection member 39 catching the hook 41 on the processus spinosus of the vertebra with the engagement groove 35 of the block 33, fastening the fixing screw 36A to the female screw portion 36B of the block 33, and firmly pressure fixing the rod portion 43 to the bottom portion of the engagement groove 35.

Further, in each of the embodiments mentioned above, the small protruding portion may be formed as a single element provided on the circular arc rod engagement portion having a sharp distal end, or may be formed as a shape having sharp distal ends separated from each other, for example, a conical convex portion. Further, the small protruding portions may be provided not only in both ends of the engagement portion but also in a plurality of positions.

According to the present invention, the small protruding portions provided on both end sides of the rod engagement portion freely engaging the rod portion of the vertebra connection member eats into the rod portion at a time of pressure fixing the rod portion to the rod portion engagement portion by the pressure fixing device, whereby it is possible to prevent the rod portion from being displaced in the longitudinal direction and on the basis of the rotation. Accordingly, the conventional problems mentioned above can be solved.

What is claimed is:

1. A rod fixing apparatus for a vertebra connecting member connecting separated vertebras, the rod fixing apparatus comprising:
   a pressure fixing device configured to pressure fix a rod portion to a circular arc rod engagement portion engaging the rod portion; and
   protruding portions configured to eat into the rod portion in both end sides of the circular arc rod engagement portion outside the pressure fixing device, the protruding portions extending in a direction substantially perpendicular to a longitudinal direction of the vertebra connecting member.

2. The rod fixing apparatus of claim 1, wherein a recess surface of the circular arc rod engagement portion between the protruding portions provided in the rod engagement portion is formed as a rough surface.

3. A rod fixing apparatus for fixing a rod of a vertebra connection member, comprising:
   a screw portion configured to be screwed into a vertebra body;
   a head portion provided with:
      a groove portion connected to the screw portion and configured to receive the rod inserted therein, and
      an engagement portion into which a fixing device configured to fix the rod is screwed; and
   small projections configured to eat into the rod, the small projections being provided on both sides of the groove portion, the small projections extending in a direction substantially perpendicular to a longitudinal direction of the rod.

* * * * *